United States Patent
Bates (10) Patent No.: US 8,062,283 B2
(45) Date of Patent: Nov. 22, 2011

(54) METHODS AND APPARATUS FOR TREATING INFARCTED REGIONS OF TISSUE FOLLOWING ACUTE MYOCARDIAL INFARCTION

(75) Inventor: Mark C. Bates, Charleston, WV (US)

(73) Assignee: Nexeon Medsystems, Inc., Charleston, WV (US)

( * ) Notice: Subject to any disclaimer, the term of this patent is extended or adjusted under 35 U.S.C. 154(b) by 0 days.

(21) Appl. No.: 12/564,844

(22) Filed: Sep. 22, 2009

(65) Prior Publication Data

US 2010/0010474 A1    Jan. 14, 2010

Related U.S. Application Data

(62) Division of application No. 10/959,289, filed on Oct. 5, 2004, now Pat. No. 7,819,856.

(51) Int. Cl.
*A61M 31/00*    (2006.01)

(52) U.S. Cl. .................................................... 604/522

(58) Field of Classification Search ............. 604/96.01, 604/101.01–101.05, 522
See application file for complete search history.

(56) References Cited

U.S. PATENT DOCUMENTS

| | | | |
|---|---|---|---|
| 5,423,744 A | 6/1995 | Gencheff et al. | |
| 5,655,548 A | 8/1997 | Nelson et al. | |
| 5,695,457 A | 12/1997 | St. Goar et al. | |
| 5,772,629 A | 6/1998 | Kaplan | |
| 5,868,703 A | 2/1999 | Bertolero et al. | |
| 6,068,638 A | 5/2000 | Makower | |
| 6,120,520 A | 9/2000 | Saadat et al. | |
| 6,432,119 B1 | 8/2002 | Saadat | |
| 6,805,860 B1* | 10/2004 | Alt ................................ | 424/93.7 |
| 7,363,072 B2* | 4/2008 | Movahed ....................... | 600/431 |
| 2003/0191449 A1 | 10/2003 | Nash et al. | |
| 2004/0258670 A1* | 12/2004 | Laughlin et al. ........... | 424/93.21 |
| 2005/0015048 A1* | 1/2005 | Chiu et al. ................ | 604/101.04 |
| 2005/0113631 A1 | 5/2005 | Bolling et al. | |

FOREIGN PATENT DOCUMENTS

WO    WO 99/60941    12/1999

* cited by examiner

*Primary Examiner* — Nicholas D Lucchesi
*Assistant Examiner* — Weng Lee
(74) *Attorney, Agent, or Firm* — Jones Day; Nicola A. Pisano; Christopher C. Bolten (57) ABSTRACT

Apparatus and methods are provided for treating an infracted region of myocardium following acute myocardial infarction by reducing the rate of blood flow through infracted region, and then injecting a solution containing stem cells, endothelial progenitor cells or mediators of stem cell mobilization, migration and attachment into the effected region so that the stem cells become embedded therein and promote tissue regeneration. In a first embodiment, delivery of the stem cells, endothelial progenitor cells or mediators of stem cell mobilization, migration and attachment is accomplished using a catheter that relies upon antegrade flow through the coronary artery and a flow control catheter placed in the coronary sinus. In an alternative embodiment, the delivery catheter delivers the stem cells in a retrograde manner through the coronary sinus, and the delivery catheter further comprises an occlusion balloon for controlling outflow through the coronary sinus ostium.

11 Claims, 5 Drawing Sheets

METHODS AND APPARATUS FOR TREATING INFARCTED REGIONS OF TISSUE FOLLOWING ACUTE MYOCARDIAL INFARCTION

This application is a divisional under 35 U.S.C. §120 of U.S. patent application Ser. No. 10/959,289, filed Oct. 5, 2004 now U.S. Pat. No. 7,819,856 and entitled "Methods and Apparatus for Treating Infarcted Regions of Tissue Following Acute Myocardial Infarction," the entire contents of which are incorporated by reference herein.

FIELD OF THE INVENTION

The present invention relates to apparatus and methods for injecting and embedding autologous body material, including stem cells, endothelial progenitor cells or mediators of stem cell mobilization, migration and attachment into an infracted region of the patient's heart.

BACKGROUND OF THE INVENTION

Myocardial infarction is caused by an abrupt occlusion of a coronary artery resulting in interruption of circulation to the affected muscle. It is now known that most myocardial infarctions occur when a blockage in the coronary artery ulcerates creating a milieu for clot formation. The cause of this change in plaque morphology (ulceration) is unclear but may be related to an inflammatory cascade or some other yet to be determined "trigger". The term now used to describe this transition in coronary lesion morphology preceding myocardial infarction is "vulnerable plaque". Rarely coronary artery occlusion may be caused by clot from a remote location (paradoxical embolic event from a deep venous thrombosis or migration of clot from an left ventricular thrombosis). Even less common is embolic septic emboli from valve infections or spontaneous coronary dissection In either of the foregoing scenarios, once the blockage occurs, the portions of the heart muscle nourished by the effected artery becomes ischemic and cell death or "necrosis" begins within minutes. If the blockage can be opened quickly, e.g., generally in less than 15 minutes, the infracted region may continue to perform without degraded function. Accordingly, great urgency is required in resolving a blockage once it is formed.

As is well-known, most tissue in the human body originates from undifferentiated cells known as stem cells. These fundamental building blocks differentiate into specific target parenchymal tissue based on hormonal and other signals. Scientific evidence suggests that stems cells or endothelial progenitor cells injected into a target tissue will differentiate into the cell line of that specific tissue. This feature is of particular interest in treating conditions involving organs that cannot regenerate, such as the heart.

It has been postulated that it may be possible to improve function of an infracted region of heart muscle by injecting stem cells or endothelial progenitor cells into the effected region as soon as the blockage is resolved. Unfortunately, conventional methods of separating stem cells from autologous material, such as bone marrow, typically require several hours of laboratory processing and culturing—far too long to provide effective near-term treatment for an acute myocardial infarction.

Since stem cells and endothelial progenitor cells have been observed in the circulation, it also may be beneficial to inject mediators of stem cell mobilization, migration and attachment. For example, Granulocyte-stimulating factor (GSF) and stem cell factor (SCF) mobilize stem cells from the bone marrow may be introduced into circulation. Vascular endothelial growth factor (VEGF) and stromal-cell derived factor-1 (SDF-1) causes release of homing factors that may bring circulating progenitor cells to the infracted myocardium to assist in repair.

In addition, it has been observed that blood vessels within ischemic tissue tend to dilate. Accordingly, even where direct injection of stem cells into the cardiac vasculature is possible, such a process would be impractical after the blockage has been opened, as the dilated myocardial blood vessels would permit the injected stem cells to be swept through the vessels so quickly that only a small percentage of the stem cells could embed in the tissue.

In view of the aforementioned limitations of previously-known systems and methods, it would be desirable to provide apparatus and methods for treating myocardial infarction by controlling the rate of blood flow through the vessels of infracted tissue during introduction of stem cells into the region.

It would further be desirable to provide apparatus and methods for treating myocardial infarction by occluding the coronary sinus, and then injecting stem cells into a coronary artery.

It also would be desirable to provide apparatus and methods for treating myocardial infarction by inducing retrograde blood flow within the coronary sinus, and then injecting stems cells into the coronary sinus.

It still further would be desirable to provide apparatus and methods for treating myocardial infarction using direct injections of autologous material, e.g., such as bone marrow aspirants, into the cardiac vasculature to promote tissue regeneration in an infracted region of the myocardium.

It also would be desirable to provide apparatus and methods for inducing retrograde blood flow within the coronary venous vasculature that do not require an external power source, but instead may be driven by naturally-occurring pressure gradients within the patient's body.

SUMMARY OF THE INVENTION

In view of the foregoing, it is an object of the present invention to provide apparatus and methods for treating myocardial infarction by controlling the rate of blood flow through the vessels of infracted tissue during introduction of stem cells, endothelial progenitor cells or mediators of stem cell mobilization, migration and attachment into the region.

It is another object of this invention to provide apparatus and methods for treating myocardial infarction by occluding the coronary sinus, and then injecting stem cells, endothelial progenitor cells or mediators of stem cell mobilization, migration and attachment into a coronary artery.

It is also an object of the present invention to provide apparatus and methods for treating myocardial infarction by inducing retrograde blood flow within the coronary sinus, and then injecting stems cells, endothelial progenitor cells or mediators of stem cell mobilization, migration and attachment into the coronary sinus.

It is a further of this invention to provide apparatus and methods for treating myocardial infarction using direct injections of autologous material, e.g., such as bone marrow aspirants, into the cardiac vasculature to promote tissue regeneration in an infracted region of the myocardium.

It is still another object of this invention to provide methods and apparatus for inducing retrograde blood flow within the coronary venous vasculature that do not require an external power source, but instead may be driven by naturally-occurring pressure gradients within the patient's body.

These and other objects of the invention are accomplished by providing apparatus and methods for treating acute myocardial infarction ("acute MI") using injections of autologous material to promote tissue regeneration. As noted above, during acute MI the permeability of the infracted zone increases and capillaries and vessels within the zone dilate. After the blockage is opened, it may be impractical to inject stem cells or other materials into the region because blood flow through the dilated vessels would sweep away injected stem cells so quickly that only a small percentage of the stem cells would embed in the region.

In accordance with the principles of the present invention, apparatus and methods are provided to enhance the residence time of stem cells injected in the effected region, comprising a delivery catheter and a balloon for partially or completely occluding outflow through the coronary sinus. In a first embodiment, the delivery catheter delivers the stem cells via antegrade flow, while a flow control catheter partly or completely blocks outflow through the coronary sinus ostium. In an alternative embodiment, the stem cells are delivered in a retrograde manner through the coronary sinus using an arterial shunt.

In a first embodiment, following angioplasty to open the blockage, a delivery catheter is inserted via a femoral artery into a desired coronary artery, such as the left anterior descending coronary artery. The delivery catheter is used to deliver a solution of containing autologous or donor stem cells, endothelial progenitor cells or mediators of stem cell mobilization, migration and attachment into the artery. The flow control catheter comprises a balloon-tipped catheter configured to occlude the coronary sinus, so that outflow through the coronary sinus ostium is controlled to a desired level during delivery of the material from the delivery catheter. In this manner, passage of blood through the infracted myocardium may be substantially slowed or arrested, thereby increasing stem cell residence time and enhancing uptake in the affected region.

Additionally, the delivery catheter may include an occlusion balloon configured to be disposed just inside the ostium of the target coronary artery. Following deflation of the occlusion balloon of the flow control catheter, blood within the coronary sinus may be aspirated through the delivery catheter, thereby ensuring that any non-embedded material does not embolize. After the stem cells embed in the infracted zone, and the residual material is aspirated from the artery, both the delivery catheter and the flow control catheter are removed, thereby restoring antegrade blood flow.

In an alternative embodiment, the delivery catheter comprises an outlet end that is disposed via a femoral vein into the coronary sinus. The delivery catheter is coupled to an arterial line that is placed in the patient's femoral artery. Due to naturally-occurring pressure gradients, blood flows from the higher pressure femoral artery to the lower pressure coronary sinus, inducing at least some retrograde flow through the venous vasculature. An occlusion balloon disposed on the outlet end of the delivery catheter may be selectively actuated to occlude outflow through the coronary sinus ostium.

The delivery catheter and optionally, the arterial line, includes an injection port to permit autologous material to be added to the blood infused into the coronary sinus. Because outflow through the coronary sinus ostium is occluded, blood perfused into the coronary sinus will migrate through the thebesian system, causing stem cells to embed in the myocardium and promote tissue regeneration. After a suitable period has elapsed, the inlet end of the delivery catheter may be uncoupled from the arterial line to permit any residual material to be aspirated from the coronary sinus via the delivery catheter. The occlusion balloon then is deflated and the outlet end of the delivery catheter removed from the coronary sinus.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
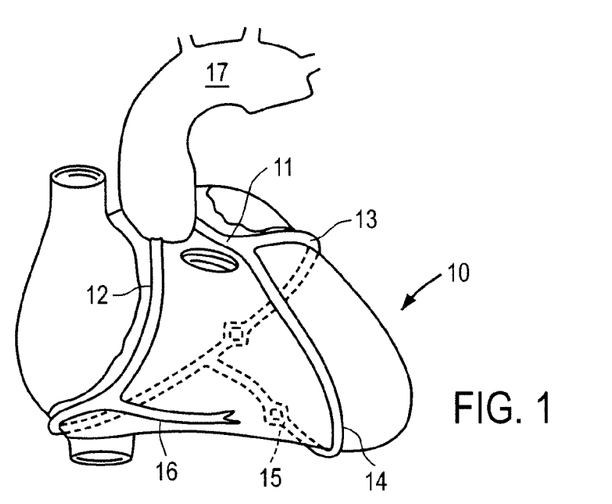
FIG. 1 is a partial perspective view of a human heart illustrating the coronary arteries.
Figure 2:
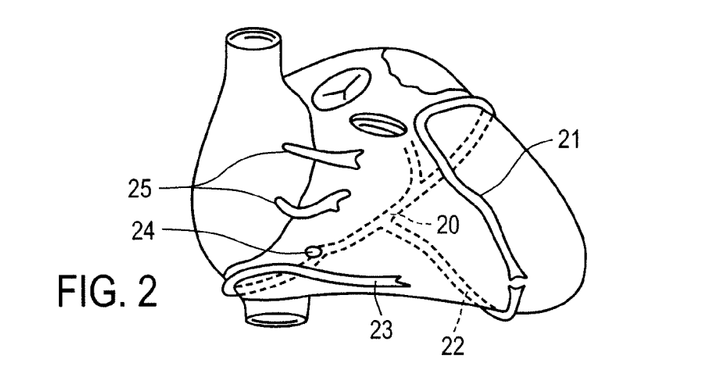
FIG. 2 is a partial perspective view of a human heart illustrating the cardiac veins.
Figure 3:
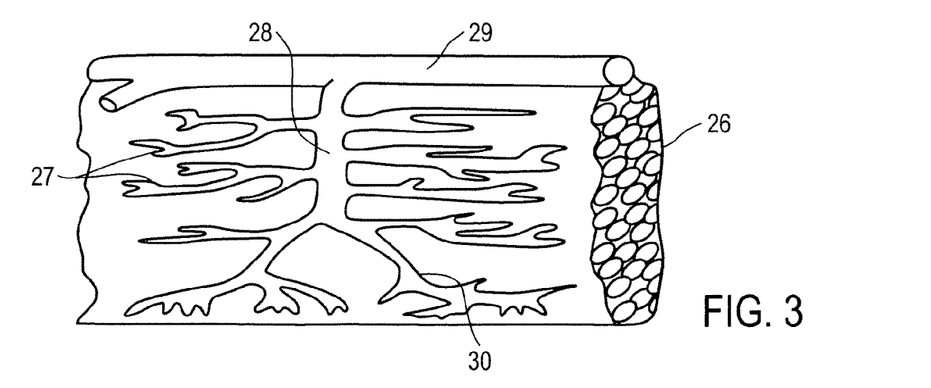
FIG. 3 is a sectional view of the myocardium, showing certain components of the cardiac venous system.

FIGS. 1 to 3 depict the coronary arterial and venous systems of a human heart. In FIG. 1, the myocardium of heart 10 is nourished by left coronary artery 11 and right coronary artery 12. Left coronary artery 11 comprises circumflex branch 13 and left anterior descending coronary artery 14; right coronary artery 12 comprises descending posterior branch 15 and marginal branch 16. Left and right coronary arteries 11 and 12 emanate from aorta 17.

Referring to FIG. 2, the cardiac venous system of heart 10 comprises coronary sinus 20, which provides drainage for great cardiac vein 21, middle cardiac vein 22, and small cardiac vein 23. Deoxygenated blood flowing into coronary sinus 20 exits via coronary sinus ostium 24 into the right atrium. The venous system further includes anterior cardiac veins 25 that drain directly into the right atrium.

With respect to FIG. 3, myocardium 26 has a lattice of capillaries 27 that drain deoxygenated blood into intramyocardial veins 28. From myocardial veins 28, a fraction of the blood drains into the cardiac veins via subepicardial veins 29, while the remainder passes through Thebesian veins 30 directly into the atrial and ventricular cavities. Approximately 70% of the deoxygenated blood is drained through the coronary sinus, while the remaining 30% is drained in about equal proportions into the left and right atria and ventricles via the lymphatic system and Thebesian veins. When individual components of the venous system (i.e., the coronary sinus, lymphatic system and Thebesian veins) are occluded, the flow redistributes itself through the remaining unoccluded channels. In addition, it has been observed that adequate drainage of deoxygenated blood can be provided by the lymphatic system and the Thebesian veins even when the coronary sinus is totally occluded.

The coronary arteries are formed of resilient tissue fibers that withstand the peak pressures typically generated in the left ventricle during cardiac systole, generally up to about 114 mm Hg. By contrast, the tissue fibers of the cardiac veins are much less resilient than those of the coronary arterial system, with peak pressures in the coronary sinus generally in a range of 6-10 mm Hg.

Figure 4:
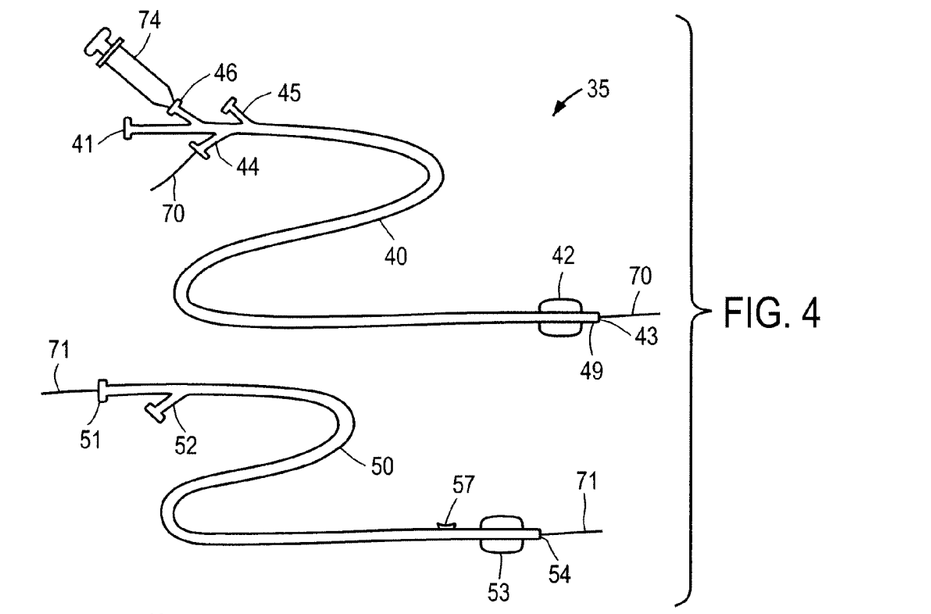
FIG. 4 is a side view of apparatus of the present invention, including a delivery catheter and a flow control catheter.
Figure 5A:
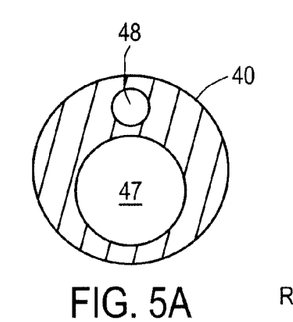
FIGS. 5A and 5B are, respectively, a cross-sectional view taken along line 5B-5B of the delivery catheter of FIG. 4 and a cross-sectional view taken along line 5B-5B of the flow control catheter of FIG. 4.
Figure 5B:
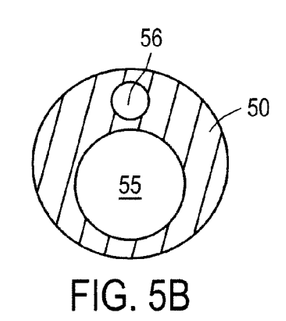

Referring now to FIGS. 4 and 5, apparatus constructed in accordance with the principles of the present invention is described. Apparatus 35 comprises delivery catheter 40 for injecting donor stem cells, endothelial progenitor cells and mediators of stem cell mobilization, migration and attachment or autologous material, into the myocardial vasculature and flow control catheter 50 for controlling the rate of flow of blood exiting the coronary sinus.

Delivery catheter 40 includes proximal end having inlet port 41 and a distal end including occlusion balloon 42 and outlet port 43. Delivery catheter 40 further includes guide wire port 44, balloon inflation port 45 and injection port 46. As shown in FIG. 6A, delivery catheter 40 includes lumen 47, which couples inlet port 41, guide wire port 44 and injection port 46 to outlet port 43. Lumen 48 couples inflation port 45 to the interior of occlusion balloon 42. Inlet port 41 is configured to be coupled to a blood pump; the distal end of delivery catheter 40 includes atraumatic tip 49 that configured facilitate insertion into a coronary artery along guide wire 70. Injection port 46 may be configured to accept conventional syringe 74 to introduce a solution containing stem cells or autologous material into blood passing through lumen 47 of the delivery catheter, or alternatively may include a luer fitting that enables connection to an infusion pump.

Flow control catheter 50 includes a proximal end having guide wire inlet port 51 and inflation port 52, and a distal end having occlusion balloon 53 and guide wire outlet port 54. As shown in FIG. 5B, lumen 55 extends between the guide wire inlet portion 51 and guide wire outlet port 54, while lumen 56 coupled inflation port 52 to the interior of occlusion balloon 53. Lumen 55 enables flow control catheter 50 to be advanced along pre-placed guidewire 71 so that occlusion balloon 53 may be disposed in a patient's coronary sinus to selectively occlude outflow through the coronary sinus ostium. Optional flow sensor 57, e.g., a piezoelectric ultrasound element, may be disposed on catheter 50 proximal of balloon 53 to monitor the flow of blood passing through the coronary sinus ostium into the vena cava.

Delivery catheter 40 and flow control catheter 50 are designed for use together to permit a solution containing autologous or donor stem cells, endothelial progenitor cells and mediators of stem cell mobilization, migration and attachment or autologous material including stem cells, to be introduced into a patient's infracted myocardium promptly after the blockage resulting from an acute MI is opened. In accordance with the principles of the present invention, flow control catheter slows drainage of blood through the coronary venous vasculature. In this manner, stem cells or other autologous material injected from syringe 74 into the artery of the infracted tissue via delivery catheter 40 will have a slower transit time through the tissue, with enhanced likelihood that the material will become imbedded in the effected tissue.

Alternatively, delivery catheter 40 may be used to enhance oxygenation of the myocardium before the coronary artery is opened. In this manner, the apparatus of the present invention may be deployed and utilized to reduce further myocardial injury and establish retrograde flow prior to the introduction of biologic material into the target region.

Figure 6:
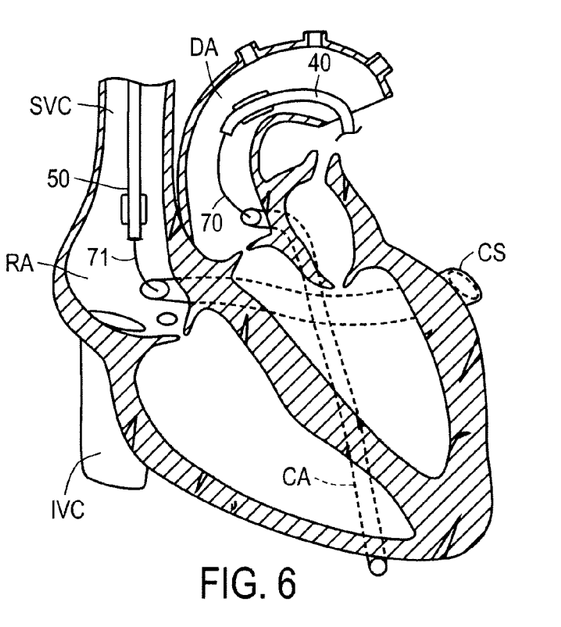
FIG. 6 is a sectional view of a human heart showing the placement of the apparatus of the present invention.

More specifically, with reference to FIG. 6, a method of using catheters 40 and 50 to treat myocardial infarction resulting from blockage-induced acute ischemia is described. After a patient suffering from acute MI arrives at a hospital, angioplasty or other another appropriate interventional procedure may be performed on an urgent basis using a balloon catheter inserted along guide wire 70 inserted into coronary artery CA. Once the blockage in coronary artery CA has been located and removed, the balloon catheter is withdrawn, and guide wire 70 is left in position. Delivery catheter 35 then is advanced along guide wire 70 until balloon 42 is disposed in coronary artery CA at a location proximal of the infracted tissue.

Guide wire 71 is inserted into the patient's coronary sinus CS via a route through either superior vena cava SVC or inferior vena cava IVC. In FIG. 6, guide wire 71 illustratively is advanced through the axillary and subclavian veins (not shown) and into right atrium RA via superior vena cava SVC. Flow control catheter 50 is advanced along guide wire 71 until balloon 53 is disposed just inside coronary sinus ostium O. Balloon 53 is inflated to occlude or partially occlude the coronary sinus ostium and create backpressure in the coronary venous vasculature that slows the drainage of blood through the myocardium. Balloon 53 may be especially configured to be retained in the coronary sinus ostium, for example, by including a roughened exterior surface that enhances adhesion to the wall of the coronary sinus ostium.

A solution containing autologous or donor stem cells, endothelial progenitor cells and mediators of stem cell mobilization, migration and attachment or alternatively containing filtered autologous bone marrow aspirant, is then injected from syringe 74 into the artery via outlet port 43 of delivery catheter 40. Catheters 40 and 50 may remain deployed for a predetermined period of time to permit the injected material to become embedded in the infracted tissue. Balloons 42 and 53 of the respective catheters 40 and 50 then may be deflated, and the catheters removed to permit normal antegrade flow to become re-established.

In this manner, passage of blood through the infracted myocardium may be substantially slowed or arrested, thereby increasing stem cell residence time and enhancing uptake in the affected region. The degree of occlusion provided by flow control catheter 50 may be adjusted to control outflow of blood through the coronary sinus ostium, and flow control catheter 50 may further include a flow sensor disposed on the exterior of the catheter 50 proximal of balloon 53, to monitor the rate of blood outflow through the partially occluded coronary sinus ostium.

Alternatively, in accordance with another aspect of the present invention, it may be desirable to maintain occlusion of the coronary sinus for a predetermined period of time, e.g., to permit uptake of the stem cells in the infracted tissue, followed by aspiration of the injected material from the artery. This may be accomplished, for example, by drawing suction on port 41 of delivery catheter 40 while deflating balloon 53 of delivery catheter 50. In this manner, a reverse flow may be established in the coronary artery and connected venous vasculature. Any unembedded injectate accordingly may be aspirated from the coronary vasculature, thereby ensuring that the material does not embolize or otherwise escape into systemic circulation. Once a sufficient quantity of blood has been aspirated, balloon 42 of delivery catheter 40 may be deflated. Catheters 40 and 50 then may be removed, permitting normal antegrade flow to become reestablished.

Figure 7:
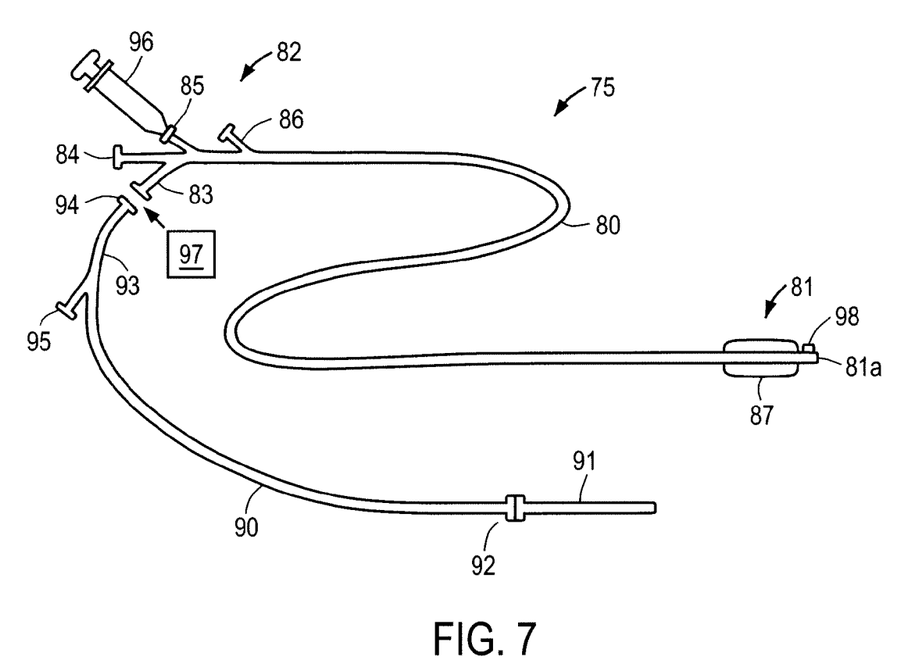
FIG. 7 is a perspective view of an alternative embodiment of the apparatus of the present invention.
Figure 8:
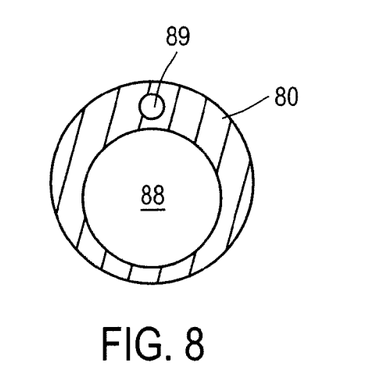
FIG. 8 is a sectional view of the delivery catheter of FIG. 7 taken along view line 8-8 of FIG. 7.

Referring now to FIGS. 7 and 8, an alternative embodiment of apparatus constructed in accordance with the principles of the present invention is described. As described herein below, apparatus 75 combines certain of the features of catheters 40 and 50, but instead employs retrograde flow through the coronary vasculature to embed stem cells endothelial progenitor cells and mediators of stem cell mobilization, migration and attachment in an infracted region of tissue, rather than antegrade flow as in the system of FIG. 4.

Apparatus 75 comprises delivery catheter 80 and arterial line 90. Delivery catheter 80 includes distal end 81, which is configured to be placed in a patient's coronary sinus, and proximal end 82, which includes inlet port 83 to be coupled to arterial line 90. Arterial line 90 includes arterial cannula 91 at distal end 92 that is configured to be placed in a patient's femoral artery, and proximal end 93, which includes luer-type fitting 94 for coupling the proximal end of the arterial line to inlet port 83 of the delivery catheter. Arterial line 90 further may include optional injection port 96, for purposes described herein below.

Proximal end 82 of delivery catheter 80 further includes guide wire insertion port 84, injection port 85 and balloon inflation port 86. Distal end 81 includes outlet port 81a and compliant balloon 87 that is configured to be inserted into, and partially or fully occlude, a patient's coronary sinus. Outlet port 81a, inlet port 83, guide wire insertion port 84 and injection port 85 all communicate with lumen 88 of the delivery catheter (see FIG. 8), while balloon inflation port 86 communicates with the interior of balloon 87 via inflation lumen 89.

When apparatus 75 is emplaced in a patient, a positive pressure gradient will be established between distal end 92 of arterial line 90 and distal end 81 of delivery catheter, thus causing retrograde flow through the venous vasculature. This flow will in turn result in a greater portion of the blood draining through the Thebesian system, as described hereinabove with respect to FIG. 3.

In accordance with this aspect of the present invention, syringe 96 is coupled to injection port 85 to inject a solution containing autologous or donor stem cells into blood flowing through lumen 88. In this manner, the stem cells endothelial progenitor cells and mediators of stem cell mobilization, migration and attachment may be carried into the venous vasculature and then become embedded in the infracted myocardium. Alternatively, an infusion pump may be substituted for syringe 96 to provide a metered amount of stem cell endothelial progenitor cells and mediators of stem cell mobilization, migration and attachment injectate over a predetermined period of time.

As yet a further alternative, optional blood pump 97, e.g., a peristaltic pump, may be connected to inlet port 83 of delivery catheter 80 and proximal end 93 of arterial line to assist in establishing retrograde flow through the coronary venous vasculature. In this case, pressure sensor 98, or a pressure sensing lumen, may be mounted on distal end 81 distal of balloon 87 to measure the pressure in the coronary sinus. If a pressure-sensing lumen is provided, it may be coupled via a side port of catheter 80 to an external transducer that permits pressure in the coronary sinus to be measured. Thus, for example, a sudden drop in the observed pressure could indicate that the balloon had deflated or migrated out of the coronary sinus.

In either of the foregoing configurations, the output of the means for measuring pressure in the coronary sinus may be used to control pump 97 to reduce the risk of edema of the coronary veins. As a still further alternative, pump 97 may be substituted for arterial line 90 in its entirety, with the blood supplied from blood bags filled with autologous or donor blood.

Operation of apparatus 75 of FIG. 7 to treat myocardial infarction resulting from blockage-induced acute ischemia in accordance with the principles of the present invention is described. After a patient suffering from acute MI arrives at a hospital, angioplasty or other another appropriate interventional procedure may be performed on an urgent basis using conventional methods. Once the blockage in the coronary artery has been located and removed, arterial cannula 91 is placed in a conveniently located artery, such as the femoral artery. Alternatively, the apparatus of FIG. 7 may be placed in the coronary sinus ostium prior to opening of the blockage to enhance perfusion of the myocardium while the blockage is located and removed, thereby reducing further myocardial injury.

In either of the foregoing cases, a guide wire is inserted into the patient's coronary sinus via a route through either the superior vena cava or inferior vena cava, for example, through the axillary and subclavian veins and into right atrium via superior vena cava. Delivery catheter 80 is advanced along the guide wire until balloon 87 is disposed just inside the coronary sinus ostium. Balloon 87 is inflated to occlude or partially occlude the coronary ostium and create a backpressure in the coronary venous vasculature that slows the drainage of blood through the venous vasculature. After the air is cleared from lumen 88, e.g., by permitting backbleed through guide wire port 84, fitting 94 of arterial line 90 is coupled to inlet port 83 of delivery catheter 80 to induce retrograde flow in the coronary venous vasculature. Due to naturally-occurring pressure gradients, blood flows from the higher pressure femoral artery to the lower pressure coronary sinus, thereby inducing retrograde flow through the venous vasculature.

A solution containing autologous or donor stem cells, endothelial progenitor cells or mediators of stem cell mobilization, migration and attachment or alternatively containing autologous bone marrow aspirant, is then injected from syringe 96 into the coronary veins via lumen 88 and outlet port 81a of delivery catheter 80. Delivery catheter 80 may remain deployed for a predetermined period of time to permit the injected material to become embedded in the infracted tissue. Balloon 87 then may be deflated, and the catheter removed to permit normal antegrade flow to become re-established through the coronary veins.

As for the preceding embodiment, balloon 87 of apparatus 75 of FIG. 7 substantially slows or arrests the flow of blood through the infracted myocardium, thereby increasing stem cell, endothelial progenitor cells or mediators of stem cell mobilization, migration and attachment residence time and enhancing uptake in the affected region. The degree of occlusion provided by balloon 87 may be adjusted to control outflow of blood through the coronary sinus ostium, and distal end 81 of the delivery catheter further may include a flow sensor disposed proximal of balloon 87 to monitor the outflow rate.

Alternatively, it may be desirable to maintain occlusion of the coronary sinus for a predetermined period of time, e.g., to permit uptake of the stem cells in the infracted tissue, followed by aspiration of the injected material from the venous vasculature. This may be accomplished, for example, by uncoupling arterial line 90 from inlet port 83, and then drawing suction on port 83 to induce antegrade flow through the venous vasculature. Any unembedded injectate accordingly may be aspirated from the coronary vasculature, thereby ensuring that the material does not embolize or otherwise escape into systemic circulation. Once a sufficient quantity of blood has been aspirated, balloon 87 of delivery catheter 80 may be deflated and catheter 80 may be removed.

Figure 9:
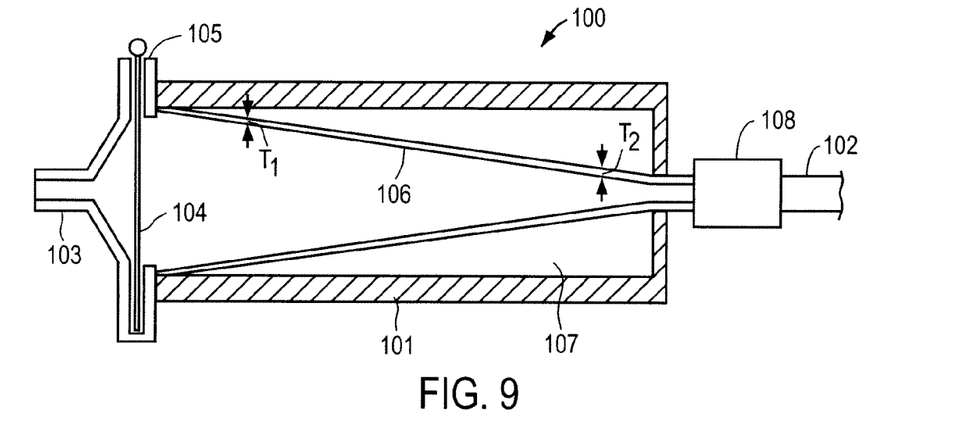
FIG. 9 is a side-sectional view of a pressure-driven pump of the present invention suitable for use with the apparatus of FIG. 7.

Referring now to FIG. 9, a pressure-driven pump suitable for use with apparatus 75 of the present invention is described. Pump 100 may be coupled to apparatus 75 between fitting 94 of the arterial line and inlet port 83 of delivery catheter 80. In accordance with the principles of the present invention, pump 100 is configured to store pressure energy during systole, and release that pressure energy during diastole. In particular, because during systole the heart muscle contracts, it is hypothesized that it may be difficult to inject stem-cell laden blood, endothelial progenitor cells or mediators of stem cell mobilization, migration and attachment into the venous vasculature during that portion of the cardiac cycle. Pump 100 therefore stores kinetic energy from the pressure wave provided from the blood passing through arterial line 90, and releases that energy during diastole, when the pressure differential is expected to be more favorable to retrograde flow through the cardiac veins. As will of course be understood, pump 100 may be directly substituted for pump 96 of FIG. 7.

In FIG. 9, pump 100 includes rigid housing 101 having inlet 102 and outlet 103. Filter element 104 is slidably disposed in housing 101 through leak-proof slot 105. Elastomeric conical member 106 is disposed in fluid communication between inlet 102 and outlet 103, and includes wall 106 having a graded thickness over its length that varies between $T_1$ and $T_2$, with $T_1$ being the thinnest portion. The thickness of the wall is selected so that wall deflects outward in response to predetermined internal pressures and may do so in a series of discrete steps, e.g., at 50, 80, 110, 160 and 200 mm Hg.

Space 107 within housing 101 surrounding conical member 106 may be evacuated, or alternatively, may include vents that permit conical member to deflect without a corresponding pressure increase in the air in space 107. In a still further alternative embodiment, space 107 may be pressurized to a desired pressure using a compressible gas, such as air. In this case, the pressure in space 107 may be selected or adjusted on a patient-by-patient basis to maximize efficiency of pump 100. One-way valve 108, which may be a conventional flap or duck-bill valve, opens during systole and closes during diastole so that conical member 106 remains pressurized during diastole.

Figure 10:
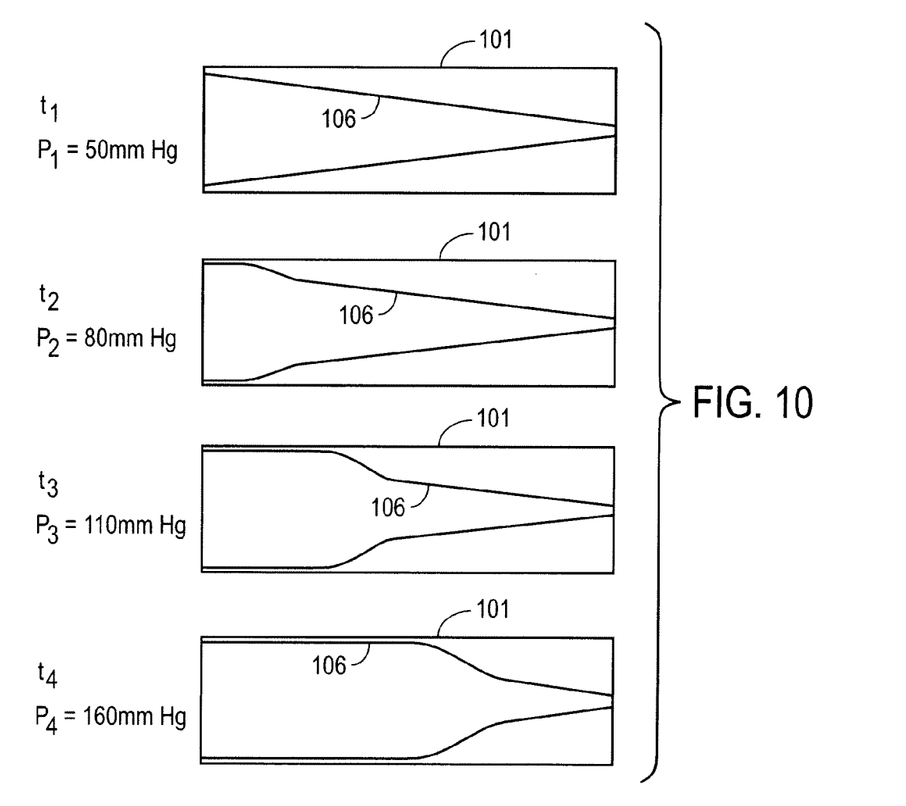
FIG. 10 is a schematic illustration showing deflection of the conical member of FIG. 9 responsive to the systolic pressure wave communicated through the arterial line.

Pump 100 operates as follows: During systole, blood received from arterial line 90 enters the interior of conical member 106 via inlet 102 and one-way valve 108. Because the myocardium contracts during systole, the pressure differential between inlet 102 and outlet 103 may be relatively small. However, in accordance with one aspect of the present invention, conical member 106 will begin deflecting outward starting at the thinnest region $T_1$. As the pressure continues to rise within the interior of conical member 106, additional regions deflect outward, thereby storing the kinetic energy of the pressure wave into potential energy corresponding to displacement of the wall of conical member 106. FIG. 10 is a schematic illustration of exemplary deflection of regions of conical member 106 at times $t_1$ through $t_4$ and corresponding pressures $P_1$ through $P_4$ during systole.

Once the diastolic portion of the cardiac cycle begins, pressure in the venous vasculature is expected to drop off quickly. This in turn permits the potential energy stored in deflection of conical member 106 to be transformed into kinetic energy in the form of a delayed pressure wave, which drives blood from the interior of conical member 106 through outlet 103 and into the venous vasculature. Over several cardiac cycles, the pressure wave provided by pump 100 assists in establishing and maintaining retrograde in the cardiac venous vasculature. As will be seen, pump 100 therefore serves as a mechanism to temporally shift the systolic pressure wave encountered in the femoral artery to the diastolic portion of the myocardial cycle.

Filter 104 of pump 100 preferably comprises a pre-selected pore size, such as 200 microns, and serves to trap emboli or clots carried in the blood received from arterial line 90. In addition, if optional injection port 95 of arterial line 90 is used to inject the solution containing the stem cells endothelial progenitor cells or mediators of stem cell mobilization, migration and attachment into the blood transfused into the coronary venous vasculature, filter 104 may be used to trap unwanted particles from entering the patient's circulation.

For example, typically there will be insufficient time to culture autologous stem cells prior to onset of an acute myocardial infarction, since such events are by definition unpredictable. In accordance with one aspect of the present invention, it is contemplated that after the blockage is removed from the effected coronary artery, raw bone marrow may be aspirated from the patient's iliac crest. Apparatus 75 is then positioned as described above, and the bone marrow aspirant may be directly injected into the blood flowing through arterial line 90 using injection port 95. Raw bone marrow aspirant typically will contain some material that should not be injected into the vasculature (fat particles, bone stromal material, etc.). Filter 104 may be configured to filter out these unwanted components of the bone marrow, while permitting the stem cells endothelial progenitor cells and mediators of stem cell mobilization, migration and attachment to be carried into, and become embedded in, the infracted portion of the myocardium via delivery catheter 80.

Figure 11:
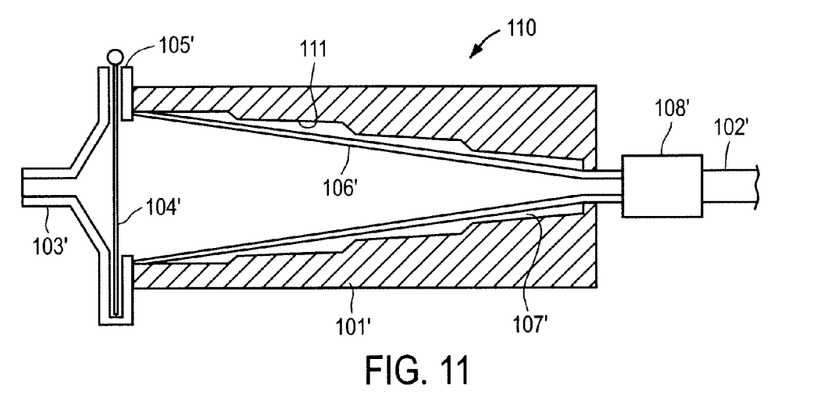
FIG. 11 is a side-sectional view of an alternative embodiment of the pressure-driven pump of FIG. 9.

With respect to FIG. 11, an alternative embodiment of a pump for shifting a pressure wave from the systolic portion to diastolic portion of the cardiac cycle is described. Pump 110 is similar in construction to pump 100 of FIG. 9; like-primed numbers indicate corresponding components of the embodiment of FIG. 9. In addition, pump 110 includes stepped inner surface 111 that controls deflection of conical member. In particular, stepped inner surface 111 of housing 101' limits deflection of a corresponding region of conical member 106', and may enhance manufacturability of the pump.

Figure 12:
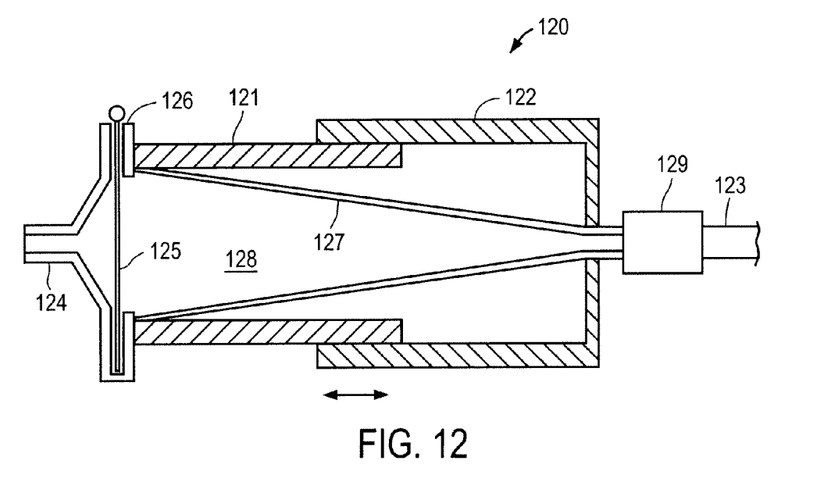
FIG. 12 is a side-sectional view of another alternative embodiment of a pressure-driven pump of the present invention.

In yet a further alternative embodiment depicted in FIG. 12, pump 120 includes a rigid housing comprising telescoping concentric tubes 121 and 122. Tube 121 includes inlet 123; tube 122 includes outlet 124. Filter 125 is replaceable inserted through leak-proof slot 126. Elastomeric member 127 defines interior space 128 disposed in fluid communication with inlet 123 and outlet 124. Elastomeric member 127 is configured to extend axially responsive to pressure buildup within space 128 during systole, and returns that energy to the blood in the form of a pressure wave during diastole. One-way valve 129 permits inflow into elastomeric member 127 during systole and closes during diastole to retain elastomeric member 127 under pressure. Operation of apparatus of pump 120 is similar to that described above for pump 100, except that the elastomeric member 127 undergoes longitudinal deflection responsive to pressure build-up rather than radial deflections in the embodiment of FIGS. 9 and 11.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A method of treating an infracted region of a patient's myocardium following an acute myocardial infarction, comprising:
    opening a blockage in a patient's coronary artery to relieve myocardial ischemia;
    providing a delivery catheter and a separate flow control catheter;
    deploying the delivery catheter in the patient's coronary vessel;
    delivering a solution containing stem cells, endothelial progenitor cells or mediators of stem cell mobilization, migration and attachment, into the coronary vessel via the delivery catheter; and
    deploying the flow control catheter in the patient's cardiac venous vasculature to partially or fully occlude blood flow through the patient's coronary ostium to create a backpressure within the patient's cardiac venous vasculature that controls a rate of blood flow through the infarcted region retaining of the stem cells in the infarcted region.

2. The method of claim 1, wherein deploying the delivery catheter in the patient's coronary vessel comprises deploying the delivery catheter in the patient's coronary artery in which the blockage was opened.

3. The method of claim 1, wherein deploying the flow control catheter in the patient's cardiac venous vasculature comprises deploying the flow control catheter in the patient's coronary sinus.

4. The method of claim 3, wherein the flow control catheter comprises a distal end including an occlusion balloon, wherein deploying the flow control catheter in the patient's cardiac venous vasculature to partially or fully occlude blood flow through the patient's coronary sinus ostium comprises inflating the occlusion balloon.

5. The method of claim 2, wherein the delivery catheter further comprises a balloon disposed adjacent to an outlet end of the delivery catheter, the method further comprising deploying the balloon.

6. The method of claim 4, further comprising, after a predetermined period after delivery of the solution containing stem cells, endothelial progenitor cells or mediators of stem cell mobilization, migration and attachment into the coronary vessel, deflating the occlusion balloon to allow blood within the coronary sinus to be aspirated through the delivery catheter.

7. The method of claim 2 further comprising monitoring a rate of blood outflow through the coronary sinus ostium.

8. The method of claim 1, wherein deploying the delivery catheter in the patient's coronary vessel comprises deploying the delivery catheter in the patient's coronary sinus.

9. The method of claim 8, wherein the delivery catheter comprises an occlusion balloon disposed on an outlet end of the delivery catheter, wherein partially or fully occluding blood flow through a patient's coronary sinus ostium comprises deploying the occlusion balloon.

10. The method of claim 8, further comprising, after a predetermined period after delivery of the solution containing stem cells, endothelial progenitor cells or mediators of stem cell mobilization, migration and attachment into the coronary vessel, aspirating blood from within the coronary sinus.

11. The method of claim 8 further comprising monitoring a pressure in the coronary sinus.

* * * * *